United States Patent [19]
Bertland, II et al.

[11] Patent Number: 5,030,720
[45] Date of Patent: Jul. 9, 1991

[54] PRES2+S HEPATITIS B VACCINE DERIVED FROM PLASMA

[75] Inventors: Alexander U. Bertland, II, Lansdale; William J. Miller, North Wales, both of Pa.

[73] Assignee: Merck & Co., Inc., Rahway, N.J.

[21] Appl. No.: 239,237

[22] Filed: Sep. 1, 1988

[51] Int. Cl.5 ............................ C07K 3/28; C07K 3/18
[52] U.S. Cl. ........................... 530/413; 530/412; 530/415; 530/418; 530/422; 530/402; 530/403; 530/405; 530/406; 530/427; 530/827; 530/830; 530/380; 424/89
[58] Field of Search .................... 530/412-413, 530/422, 427, 415-418, 830, 837, 402-403, 405-406, 380; 424/89

[56] References Cited

U.S. PATENT DOCUMENTS

| | | | |
|---|---|---|---|
| 3,636,191 | 1/1972 | Blumberg et al. | 424/89 |
| 4,017,360 | 4/1977 | Bertlandd et al. | 424/89 |
| 4,649,192 | 3/1987 | Wignendarle et al. | 424/89 |
| 4,683,293 | 7/1987 | Craig | 435/190 |
| 4,695,454 | 9/1987 | Prince et al. | 424/89 |
| 4,707,542 | 11/1987 | Fredman | 424/89 |
| 4,855,055 | 8/1989 | Lin et al. | 424/89 |
| 4,897,465 | 1/1990 | Cerdle et al. | 530/414 |

OTHER PUBLICATIONS

Meyhack et al., Chem. Abst. vol. 103, 1983, #136419w.
Wampler et al., Modern Approaches to Vaccines, ed. Chanack et al., 1984, pp. 251-256.
Damodaran et al., Biochem. Biophys. Acta 801, 1984, pp. 416-423.
Stibbe et al., J. Virol. 46 (2):626-628 (1983).
Ohnuma et al., Clin. exp. Immunol. 67:709-715 (1986).

Primary Examiner—Garnette D. Draper
Attorney, Agent, or Firm—Donald J. Perrella; Hesna J. Pfeiffer

[57] ABSTRACT

Hepatitis B PreS2+S antigen is isolated from plasma by adsorption on an affinity chromatography column, elution with a chaotropic agent and treatment with concentrated urea at an elevated temperature. The process retains all or substantially all of the preS2+S antigen.

6 Claims, No Drawings

PRES2+S HEPATITIS B VACCINE DERIVED FROM PLASMA

BACKGROUND OF THE INVENTION

The isolation of hepatitis B surface antigen from plasma and its purification and use in a vaccine to immunize against hepatitis B is known and is described, for example, in U.S. Pat. Nos. 3,636,191 and 4,017,360. Current vaccines isolated from plasma, however, do not contain the preS2 component of the hepatitis B surface antigen. An antigen containing the pre-S region would have enhanced immunogenicity relative to antigens produced by current techniques which lack this region of HBsAg.

OBJECTS OF THE INVENTION

It is, accordingly, an object of the present invention to provide a method to isolate the intact preS2+S molecule Another object is to provide a method for isolating HBsAg which does not truncate the preS2+S molecule These and other objects of the present invention will be apparent from the following description.

SUMMARY OF THE INVENTION

Hepatitis B preS2+S antigen is isolated from plasma by a process that comprises passing the plasma through an affinity chromatography column adapted to adsorb preS2+S antigen, eluting the adsorbed antigen from the column with a chaotropic agent, treating the eluted antigen with concentrated urea at an elevated temperature, and removing the urea from the treated antigen. The process retains all or substantially all of the preS2+S antigen.

DETAILED DESCRIPTION

According to the present invention, the preS2+S antigen is isolated from plasma by subjecting the plasma to immunoaffinity chromatography through a column, e.g., CNBr activated Sepharose 4B beads, which adsorbs the preS2+S antigen, followed by elution of the adsorbed molecule by treating the column with a chaotropic agent followed by dialysis. Any impurity in resulting preS2+S antigen is then inactivated by treatment with concentrated urea, i.e., urea having a concentration of from about 6 molar to about 10 molar at an elevated temperature of at least about 30° C. for a period of from about 2 hours to about 10 hours. Following the inactivation steps, the urea is removed, e.g., by dialysis. The resulting product retains 100% preS2+S antigen and/or AUSRIA activities.

A chaotropic agent contains an ion that disrupts the structure of water and reduces hydrophobic interactions. Consequently, they are effective desorbing agents. Examples of chaotropic ions are $Cl^-$, $I^-$, $ClO_4^-$, $CF_3COO^-$, $SCN^-$ OR $CCl_3COO^-$. Suitable chaotropic aqents are the alkali metal and ammonium salts of the foregoing chaotropic ions, e.g., NaCl, KCl, $NH_4Cl$, NaI, KI, $NH_4I$, $NaClO_4$, $KClO_4$, $NH_4ClO_4$, $CF_3COONa$, $CF_3COOK$, $CF_3COONH_4$, NaSCN, KSCN, $NH_4SCN$, $CCl_3COONa$, $CCl_3COOK$ AND $CCl_3COONH_4$.

The following examples illustrate the present invention without, however, limiting the same there too.

EXAMPLE 1

Human plasma positive for HBsAg, (50 ml), was mixed with goat HBsAb (10 ml) bound to CNBr activated Sepharose 4B beads (Pharmacia) and rotated for 18 hours at 4° C. The mixture was then centrifuged at 2,000–3,000×g for 10 minutes Phosphate buffer saline (PBS), 25 ml, was added to the beads. This procedure was repeated 4 times after which the beads were packed into a K9 Pharmacia column and eluted with 30 ml of 3M KSCN. The eluate is dialyzed 3 times against 1 l PBS at 4° C. for a total of 24 hours.

The dialyzed HBsAg, 1.0 ml, containing 134 mcg protein/ml was added to 0.75 g urea to obtain a urea concentration of 8M. The mixture was incubated for 0.5 hours at 37° C. The mixture then was transferred by pipette to a new bottle and the incubation continued for 3.5 hours to make certain all the sample was exposed to the 8M urea. The mixture was then dialyzed against 4× one liter of PBS. The first dialysis was carried out for 1 hour at room temperature, the second for 2 hours at 4° C., the third overnight at 4° C. and the fourth for 2 hours at 4° C. Final volume was 2 ml. The results of Lowery protein analysis, AUSRIA and preS2+S RIA on the final product are as follows:

|  | Lowry Protein (μg/ml) | AUSRIA (μg/ml) | PreS2 RIA (μg/ml) |
| --- | --- | --- | --- |
| Starting Plasma | — | 567 | 445 |
| Dialyzed Affinity Product | 134 | 141 | 72.4 |
| Dialyzed and Incubated Affinity Product | — | — | 54.5 |
| *Urea Inactivated Affinity Product | 94 | 94 | 65.8 |

The urea-inactivated antigen is obtained in essentially quantitative yield with respect to AUSRIA and preS2 + S RIA antigens.
*Urea inactivation and dialysis results in approximately a two-fold dilution which has been accounted for in the stated values.

EXAMPLE 2

Human plasma, 50 ml, positive for HBsAg, was mixed with 10 ml of HBsAb beads (goat HBsAb bound to CNBr activated Sepharose 4B beads) and rotated overnight at 4° C. The mixture was then centrifuged at 2,000–3,000×'g for 10 minutes. PBS, 25 ml, was added to the beads which were then centrifuged at 2,000–3,000× g for 10 minutes. The PBS centrifugation step was repeated 4 more times. The beads were packed into a K9 Pharmacia column, eluted with 30 ml of 3M KSCN in one batch, and dialyzed against 3×1 liter PBS at 4° C. for a total of 24 hours.

Urea, 21 g, was added to 28 ml of dialyzed HBsAq, and incubated for 0.5 hours at 37° C. The mixture then was transferred by pipette to a new bottle and the incubation continued for 3.5 hours to insure that all of the sample was exposed to the 8M urea. Next, the mixture was dialyzed against 4×1 liter of PBS following the same protocol as in example 1 with the following analytical results:

|  | Lowry Protein (μg/ml) | AUSRIA (μg/ml) | PreS2 RIA (μg/ml) |
| --- | --- | --- | --- |
| Starting Plasma | — | 409 | 95.7 |
| Dialyzed Affinity Product | 76 | 29.1 | 25.0 |
| *Urea Inactivated Affinity Product | 74 | 29.4 | 20.0 |

*Urea inactivation and dialysis results in approximately a two-fold dilution which has been accounted for in the stated values.

The urea-inactivated antigen is obtained in essentially quantitative yield with respect to the AUSRIA and preS2+S RIA antigens.

What is claimed is:

1. A method of isolating hepatitis B preS2+S antigen from plasma consisting essentially of passing plasma through an affinity chromatography column adapted to adsorb preS2+S antigen, eluting the adsorbed preS2+S antigen from the column with a chaotropic agent, then treating the eluted antigen with concentrated urea at an elevated temperature and removing the urea from the treated antigen.

2. A method according to claim 1 wherein the column comprises CNBr activated Sepharose 4B.

3. A method according to claim 1 wherein the chaotropic agent is NaCl, KCl, $NH_4Cl$, NaI, KI, $NH_4I$, $NaClO_4$, $KClO_4$, $NH_4ClO_4$, $CF_3COONa$, $CF_3COOK$, $CF_3COONH_4$, NaSCN, KSCN, $NH_4SCN$, $CCl_3COONa$, $CCl_3COOK$, OR $CCl_3COONH_4$.

4. A method according to claim 1 wherein the urea has a concentration of from about 6 molar to about 10 molar.

5. A method according to claim 1 wherein treating with urea takes place at a temperature of at least about 30° C.

6. A method according to claim 1 wherein treating with urea is continued over a period of from about 2 hours to about 10 hours.

* * * * *